(12) United States Patent
Bruederle et al.

(10) Patent No.: US 9,111,023 B2
(45) Date of Patent: Aug. 18, 2015

(54) BRIDGE APPARATUS FOR COUPLING A MEDICAL NETWORK WITH A NON-MEDICAL NETWORK

(75) Inventors: Klaus Bruederle, Moos (DE); Dietmar Dechow, Schaffhausen (CH)

(73) Assignee: STORZ ENDOSKOP PRODUKTIONS GMBH (DE)

( * ) Notice: Subject to any disclaimer, the term of this patent is extended or adjusted under 35 U.S.C. 154(b) by 383 days.

(21) Appl. No.: 13/044,244

(22) Filed: Mar. 9, 2011

(65) Prior Publication Data

US 2011/0264839 A1  Oct. 27, 2011

(30) Foreign Application Priority Data

Mar. 10, 2010  (DE) .......................... 10 2010 010 949

(51) Int. Cl.
*G06F 19/00* (2011.01)
*G06F 15/16* (2006.01)

(52) U.S. Cl.
CPC ................................. *G06F 19/3418* (2013.01)

(58) Field of Classification Search
CPC .................................................. G06F 19/3418
See application file for complete search history.

(56) References Cited

U.S. PATENT DOCUMENTS

| 2003/0131261 | A1 | 7/2003 | Hashimoto et al. | |
|---|---|---|---|---|
| 2004/0153289 | A1* | 8/2004 | Casey et al. | 702/188 |
| 2009/0002150 | A1 | 1/2009 | Zilberstein et al. | |
| 2009/0313368 | A1* | 12/2009 | Hollebeek et al. | 709/223 |
| 2010/0174229 | A1* | 7/2010 | Hsu et al. | 604/66 |

FOREIGN PATENT DOCUMENTS

| DE | 60122786 T2 | 9/2007 |
|---|---|---|
| WO | 2008001344 A2 | 1/2008 |

OTHER PUBLICATIONS

German Search Report; Application No. DE 10 2010 010 949.5; Dec. 23, 2010; 4 pages.
Strother; "Denial of Service Protection the Nozzle"; Computer Security Applications; Dec. 11, 2000; pp. 32-41.
European Search Report; Application No. EP 11 15 7307; Issued: Aug. 19, 2011; 10 pages.

* cited by examiner

*Primary Examiner* — Suraj Joshi
(74) *Attorney, Agent, or Firm* — Whitmyer IP Group LLC

(57) ABSTRACT

A bridge apparatus for coupling a medical network with a non-medical network includes a storage unit to store data from the medical network, a first interface device for coupling the storage unit with the medical network, and a second interface device for coupling the storage unit with the non-medical network. The bridge apparatus is configured to execute write-only access requests on the storage unit via the first interface device or to execute read-only access requests on the storage unit via the second interface device.

31 Claims, 2 Drawing Sheets

BRIDGE APPARATUS FOR COUPLING A MEDICAL NETWORK WITH A NON-MEDICAL NETWORK

CROSS-REFERENCE TO RELATED APPLICATIONS

The present application claims priority of German patent application No. 10 2010 010 949.5 filed on Mar. 10, 2010.

FIELD OF THE INVENTION

The present invention relates to a bridge apparatus for coupling a medical network with a non-medical network and to a method for providing data from a medical network in a non-medical network.

BACKGROUND OF THE INVENTION

In a clinic, a medical practice, or another medical institution and particularly in an operating room or another medical treatment space, several medical devices can exchange data via a medical network. Medical devices can be, for example, devices used for endoscopy, other devices for imaging or non-imaging diagnostics, surgical devices, heart-lung machines and other devices for substituting bodily functions, display screens and user interfaces for medical staff. An outage of a medical device can constitute a risk for a patient's health and life.

Despite the advantageous and desired exchange of data between medical devices, in order to avoid harmful reciprocal action between said devices, considerable expense is incurred in developing medical networks and corresponding interfaces on medical devices. To prevent disturbing impacts from sites outside the medical network, medical networks in many cases are operated as islands largely or completely isolated from the IT environment and in particular from the Internet.

However, isolation of a medical network from the Internet also has a series of disadvantages. In particular, it is desirable that medical staff that has no physical access to a device in the medical network should be able to observe or monitor parameters measured by medical devices or entered on medical devices. Also advantageous would be an evaluation of processes that are recorded or controlled by devices in the medical network, for example during an operation, in order, for instance, to analyze and optimize sequences. A purely technical monitoring of the devices in the medical network would be advantageous, for example with respect to meeting servicing deadlines and planning maintenance tasks.

SUMMARY OF THE INVENTION

An object of the present invention consists in providing an improved bridge apparatus for coupling a medical network with a non-medical network, a method for providing data from a medical network to a non-medical network, and a computer program with programming code to execute or control such a method.

This object is achieved through the content of the independent claims.

Refinements are indicated in the dependent claims.

Embodiments of the present invention are based on the idea of connecting a medical network and a non-medical network via a bridge apparatus that includes a storage unit. It is possible in the storage unit to store or file data from the medical network that can then be read by the non-medical network. In this manner, data from the medical network are made available in the non-medical network or for participants in the non-medical network, without access by the non-medical network to the medical network being required and needing permission. Thus the present invention combines all advantages of availability of data from the medical network in the non-medical network with a high degree of security for the medical network, in particular security from outage and manipulation from the non-medical network. In particular, the inventive coupling of the medical network with the non-medical network makes possible an effective prevention of a denial-of-service attack in which, owing to a high number of access requests, a user or an entire network is disabled, even including complete blocking of its functioning.

A bridge apparatus for coupling a medical network with a non-medical network includes a storage unit for storing data from the medical network, a first interface device for coupling the storage unit with the medical network, and a second interface device for coupling the storage unit with the non-medical network, so that the bridge apparatus is configured at least either to permit or execute write-only access requests to the storage unit via the first interface device or to admit or execute read-only access requests to the storage unit via the second interface device.

A bridge apparatus as described here is thus configured in particular at least either to ignore or not to execute all reading access requests to the storage unit entered or received via the first interface device or configured to ignore or not to execute all writing access requests to the storage unit entered or received via the second interface device.

Because write-only access to the storage unit is admitted or executed from the medical network and/or read-only access to the storage unit is executed or admitted from the non-medical network, an intentional or unintentional outage of the medical network from the non-medical network can be prevented. This makes possible, while strongly securing the medical network from outages from outside, an observation or monitoring of devices in the medical network or of their functioning by technical staff outside the medical installation, an observation of processes in which devices in the medical network are involved, as a basis for optimizing said processes, a tracking of processes in which devices in the medical network are involved, by trained or trainable medical staff outside the medical installation, for example for purposes of quality control or training and the like.

In a bridge apparatus as described here, in particular at least either the first interface device is exclusively configured for writing access requests to the storage unit or the second interface device is exclusively configured for reading access requests to the storage unit. For this purpose, in particular, software or firmware is configured corresponding to the bridge apparatus. Alternatively the first interface device and/or the second interface device can be configured physically so that every type of data can be transmitted only from the medical network to the storage unit of the bridge apparatus or from the storage unit to the non-medical network.

The first interface device includes, for example, a writing device for writing data from the medical network into the storage unit and a data input for coupling the writing device with the medical network. The writing device can include hardware and/or software or firmware modules. The data input includes, for example, a plug-in connection.

The second interface device includes, for example, a reading device for reading data from the storage unit and a data output for coupling the reading device with the non-medical network. The reading device can include hardware and/or software or firmware modules. The data output includes, for example, a plug-in connection.

Hardware of the writing device can be partly or completely identical with hardware of the reading device. For example, a storage control of a solid state storage unit or of an optical or magnetic mass storage unit as well as writer/reader heads of optical or magnetic mass storage units can be used simultaneously by the first interface device and the second interface device or can be simultaneously part of the writing device and part of the reading device. Alternatively, the writing device and reading device can be completely disjoint or all components of the writing device cannot be simultaneously components of the reading device.

Software or firmware modules of the writing device and reading device are, in particular, at least partly associated either with only the writing device or the reading device.

Depending on the storage unit in use, the writing device and reading device can be adjusted in many ways to the expected data rates and the desired security level with respect to their hardware components and their software or firmware modules.

A bridge apparatus as described here can be configured to store current data and historical data in the storage unit and to output them via the second interface device to the non-medical network. Current data are also referred to as live data. By means of the bridge apparatus, it is thus possible at any time from a non-medical network not just to call up values of measured or controlled parameters of devices in the medical network that are available momentarily or at a point only a few seconds or fractions of a second in the past. In addition, historical data that must be no longer available in the medical network or in its devices can be read out of the bridge apparatus or of its storage unit. This makes possible a retrospective analysis of the conditions of the devices as well as of the processes observed or controlled in the medical network. Such an analysis can be the basis for a technical and/or medical optimization by technical or medical staff. It is also possible, from historical data, to deduce information on conditions of ware of devices in the medical network that in turn can be the basis for planning and performance of service and maintenance tasks.

A bridge apparatus as described here includes, in particular, a device for providing data received via the first interface device, whereby the device is configured at least to determine either a mean or a time integral or an extreme value within a given time interval.

Providing data from the medical network in this manner makes possible a clear reduction of the volume of historical data. The required storage volume of the storage unit is thereby reduced. In addition the provision of historical data can be simplified and accelerated.

The device for providing data received via the first interface device is configured, for example, to determine or compute a median, an integral value, a maximum value, and a minimum value for every parameter recorded or controlled by the device. The series of time intervals is uninterrupted, in particular, in periods in which a predetermined device, a group of devices, or all devices in the medical network are in operation. The time intervals can be identical for all parameters of a device or for all parameters of all devices in the medical network. Alternatively, the time intervals can be different for the parameters of different devices in the medical network or for different parameters of the same device. Lengths of time intervals can be firmly predetermined or, for example, can have a variable length depending on predetermined events. For parameters that rarely change, the time intervals can be selected in such a way that no change arises within one time interval. In this case it is possible to dispense with the computation of extreme values. Time intervals of firmly predetermined duration can be selected as brief for parameters that can change frequently and/or quickly and long for parameters that can change seldom and/or slowly.

With parameters that seldom change and/or assume only a low number of different values, it is possible as an alternative to ascertain and record only the points in time at which the parameters change and the particular values existing after these points. Examples of such parameters are operating modes of devices including the switch-on or switch-off status.

Historical data provided by the device, in particular medians, extreme values, integral values, are filed in the storage unit along with information on the start and end of the particular time interval. For this purpose the storage unit, in particular, includes a database or is part of a database system. It is possible at any time for the storage unit to read from the non-medical network the historical data that were in existence in the medical network at nearly every possible time in the past. For example, for every desired time of interest, it is possible to ascertain the time interval in which it is included. Then, for this time interval, for every parameter recorded and filed in the storage unit the median, the minimum value, and the maximum value as well as the time integral value since a predetermined point of reference that lies before the time interval can be read from the storage unit and provided in the non-medical network.

An advantage of filing or recording time integral values consists in the fact that a time integral value can be determined over a fairly long period with minor difficulty as the difference between the time integral values filed in the storage unit at the end and at the beginning of the period of interest. In this manner it is possible with little difficulty and quickly to determine parameters such as a number of operating hours of a device, a required volume, or a number of rotations of a motor within a period of interest.

The storage unit of a bridge apparatus as described here can include a temporary storage unit and/or a non-temporary storage unit. The temporary storage unit is or includes, in particular, a multiple-writable storage unit with random access memory (RAM) or another solid-state storage unit. The non-temporary storage unit is or includes, in particular, a hard disk, another magnetic or optical storage medium or a solid-state drive (also termed a semiconductor drive), which includes for instance a flash-based semiconductor storage unit. The bridge apparatus is configured in particular to store, in the temporary storage device of the storage unit, current data or the value last received from the last-received parameters from the medical network, and to store or file historical data in the non-temporary storage device of the storage unit. In particular, the bridge apparatus is configured to file current data exclusively in the temporary storage device of the storage unit and historical data exclusively in the non-temporary storage device of the storage unit.

An advantage of using a storage unit with a temporary storage device and a non-temporary storage device can consist in the fact that the temporary storage device can be written in especially brief time and repeatedly, with nearly unlimited frequency, and that the non-temporary storage device is suited for durable storage of historical data even over periods without power supply.

A bridge apparatus as described here can be configured to time-stamp data received via the first interface device. Data from a device from the medical network that have already been marked with a time stamp by the device can receive an additional time stamp from the bridge apparatus. Alternatively, the time stamp of the device can be replaced by the time stamp of the bridge apparatus. The time stamp generated by the bridge apparatus ensures that all data stored in the storage unit of the bridge apparatus can be associated with a unified time axis, and prevents disturbing influences of non-synchronous clocks of devices in the medical network.

A bridge apparatus as described here can be configured to archive and/or to document data of an operation or of another medical procedure. This occurs in particular in storing historical data. The bridge apparatus can thus fulfill two functions simultaneously, namely the coupling of a medical network with a non-medical network and the archiving or documenting of data. Thus the bridge apparatus can contribute to quality control.

A bridge apparatus as described here can be configured to issue no error message into the medical network or to suppress every error message out of a predetermined group of error messages to recipients in the medical network. A great quantity of error messages in the medical network can disturb it, even to the point of completely impeding its functioning. If the bridge apparatus can be caused intentionally or unintentionally from the non-medical network to issue error messages to the medical network, this can constitute a security risk for the medical network. If, on the other hand, the bridge apparatus is configured to issue no error messages or only error messages from a predetermined group of error messages to the medical network, this risk can be excluded or at least reduced.

A method for providing data from a medical network to a non-medical network includes the following steps:

couple a bridge apparatus with the medical network via a first interface device of the bridge apparatus;

couple the bridge apparatus with the non-medical network via a second interface device of the bridge apparatus;

receive data from the medical network via the first interface device;

write the received data to a storage site of a storage unit of the bridge apparatus;

read data from the storage unit;

provide the data read from the storage unit to the second interface.

Because data received from the medical network are filed in a storage unit of a bridge apparatus and later are read out and provided to the non-medical network, a high degree of security can be combined with the advantages of coupling the medical network with the non-medical network, as in the case of the bridge apparatus described above. In particular, intentional or unintentional disruptions of the medical network from the non-medical network can be effectively suppressed.

A method as described here can in addition include at least one of the following steps:

select data from the medical network that are to be written into the storage unit, on a user interface in the medical network;

receive a "read" statement via the second interface;

discard a read statement received via the first interface device;

discard a "write" statement received via the second interface device;

review a statement received via the second interface device and discard the statement if it is not a read statement;

prepare historical data;

write historical data to a storage site of the storage unit.

In particular, the method does not foresee selecting writable data on a user interface outside the medical network.

The present invention can be implemented as a method or as a computer program with program code for performing or controlling such a method if the computer program runs on a computer or processor. In addition, the invention can be implemented as a computer program product with program code stored on a machine-readable carrier (for example, an ROM, PROM, EPROM, EEPROM, or Flash storage unit, a CD-ROM, DVD, HD-DVD, Blue-Ray disc, diskette or hard drive) or in the form of firmware to perform one of the aforementioned methods if the computer program product runs on a computer or processor. In addition, the present invention can be implemented as a digital storage medium (for example, ROM, PROM, EPROM, EEPROM, or Flash storage unit, CD-ROM, DVD, HD-DVD, Blu-Ray disc, diskette or hard drive) with electronically readable control signals that can interact with a programmable computing or processor system in such a way that one of the described methods is performed.

In addition, the present invention can be implemented as a control device, where said control device is configured to perform one of the described methods, or where said control device includes a computer program, a computer program product, or a digital storage medium as they are described in the preceding paragraph.

BRIEF DESCRIPTION OF THE DRAWINGS

Embodiments are presented in greater detail hereinafter with reference to the appended drawings, which are as follows.

DETAILED DESCRIPTION OF THE INVENTION

Figure 1:
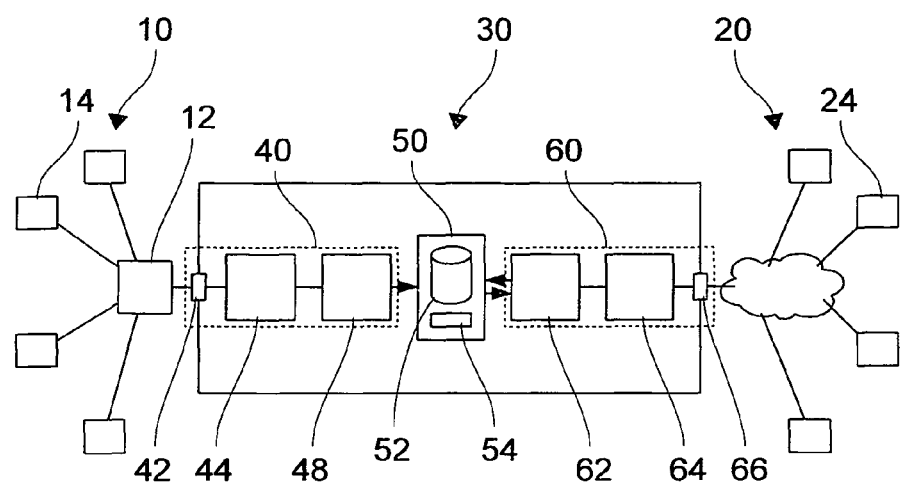
FIG. 1 shows a schematic depiction of a bridge apparatus.

FIG. 1 shows a schematic depiction of a medical network 10, a non-medical network 20, and a bridge apparatus 30 that couples the medical network 10 with the non-medical network 20. The bridge apparatus is also referred to as a device monitor service provider.

The medical network 10 includes one or more junctions 12 with which one or more devices 14 are coupled via electrical or optical signal cables or by means of electromagnetic or optical signals that are transmitted through the free space. The medical network 10 can, instead of the star-shaped topology indicated in FIG. 1, have a bus topology or any other desired topology. Examples for the devices 14 are camera controls or video cameras, light sources, control devices for motor operation and other devices for diagnostic, surgical, and/or therapeutic purposes. The medical network can be, for example, a Storz Communication Bus (SCB) corresponding to the Karl Storz concept designated as OR 1.

The non-medical network 20 includes devices 40, for example workplace computers, and can have any topology. The non-medical network 20 can include a local network, the Internet, or parts of the Internet.

The bridge apparatus 30 includes a medical area 40, a storage unit 50, and a non-medical area 60. The bridge apparatus 30 can include areas, components, functional units, and hardware and software modules that are not shown in FIG. 1 and hereinafter are not described in further detail. They include for example a power supply device for the entire bridge apparatus or several power supply devices for various elements, areas, or components of the bridge apparatus 30.

The components of the bridge apparatus 30 described hereinafter can include additional units or can be combined into greater components or units. The functions of the bridge apparatus 30 described hereinafter can be distributed among the components and modules of the bridge apparatus 30, or can be performed by the components, in other ways than as described hereinafter with reference to FIG. 1.

The medical area 40 of the bridge apparatus 30 includes a data input 42 for coupling with the medical network 10. The data input 42 includes, for example, a plug-in connection for inserting one end of an optical or electrical signal cable for connecting with the medical network 10, in particular with the junction 12. Alternatively the data input 42 includes a reception device for receiving or an emitting and receiving device for emitting and receiving electromagnetic or light signals in the infrared range.

The medical area 40 of the bridge apparatus 30 includes, in addition, a data reception device 44 with an input that is coupled with an output of the data input 42. The data reception device 44 is configured to receive data from the medical network 10 via the data input 42. Data received by the data reception device include, in particular, current values of parameters that can be selected on devices 14 in the medical network 10 or are measured or controlled by devices 14 in the medical network 10.

The data reception device 44 can be configured to subscribe to data on devices 14 in the medical network 10. The devices 14 emit the current values of subscribed parameters at each modification of the parameter, at each modification of the parameter that lies above a predetermined positive modification threshold or below a predetermined negative modification threshold, at the presence of another predetermined condition and/or at predetermined time points or at predetermined time intervals. The bridge apparatus 30 has in particular at least one operating mode in which the communication between the bridge apparatus 30 and a device 14 as required for subscribing to parameters is allowed via the data input 42. A similar way of obtaining data is also referred to in other fields of information technology as subscribing.

Alternatively or in addition, the data reception device 44 can be configured to retrieve in the medical network 10 the values of predetermined parameters at predetermined times or at predetermined time intervals or upon the existence of predetermined conditions of devices 14. Borrowing from language in other fields of information technology, this way of retrieving data is also referred to hereinafter as polling. Depending on the type of medical network 10 and its properties, in particular protocol and bandwidth, dispensing with the last-mentioned polling functionality can be considered a gain in security because intentional or unintentional pressure on the medical network 10 and its bandwidth can be prevented by frequent polling.

The data reception device 44 can be configured so that a user, via a user interface, can select data or parameters that are to be received via the data input 42 from the medical network 10, for example by subscribing or polling. The user interface includes, for example, a screen, a keyboard, and a computer mouse. The user interface can be coupled with the bridge apparatus 30 directly or via the medical network. If the user interface is coupled with the bridge apparatus 30 via the medical network 10, the data reception device 44 must at least comprise an operating mode in which the communication of the bridge apparatus 30 with the user interface as required for the selection process is allowed via the data input 42.

The data reception device 44 of the bridge apparatus 30 can, in addition, be configured to suppress each issuing or each emission of data, commands, instructions, or other information via the data input 42 into the medical network 10. The just-described polling functionality cannot be realized in this case. Alternatively, the data reception device 44 can be configured to emit only commands or instructions from a predetermined group of commands or instructions via the data output 42 into the medical network 10. In addition, the data reception device 44 can be configured to emit at predetermined time intervals at most a predetermined maximum number of commands or instructions via the data input 42 into the medical network 10. Depending on the properties of the medical network 10, the highest security against intentional or unintentional disruptions of the medical network 10 by the bridge apparatus 30 can be achieved in many cases if the data reception device 44 is configured to emit no commands or instructions via the data input 42 into the medical network 10.

The data reception device 44 can, in addition, be configured to receive only data via the data input 42. For example, the data reception device 44 can be configured to ignore commands and instructions received from the medical network 10 or all commands and instructions from a predetermined group of commands and instructions. In particular, the data reception device 44 is configured to ignore read messages received via the data input 42 from the medical network 10. Instead of ignoring or not executing instructions, the data reception device 44 can be configured to reply to instructions or commands in predetermined, secure manner. A secure answer, for example, includes a brief report independent of the instruction or command and triggering no additional action from the communication partner.

In particular, the data reception device 44 is configured to review each instruction received via the data input 42 from the medical network 10 to determine whether it is a read message and to discard or ignore the instruction or to answer it in a secure manner if it happens to be a read message.

The medical area 40 of the bridge apparatus 30 also includes a writing device 48 for writing or filing data in storage locations of the storage unit 50. A data input of the writing device 48 is coupled with a data output of the data reception device 44, and a data output of the writing device 48 is coupled with a data input of the storage unit 50.

The writing device 48 can be configured to provide data received by the data reception device 44 with a time stamp, which was generated by the writing device 48 or received by a device not shown in FIG. 1, and to write said data into the storage unit 50 with this time stamp.

In addition, the writing device 48 can be configured to write both current and historical data into the storage unit 50. Current data are in each case the most recent values of parameters received via the data input 52 and the data reception device 44. Historical data are the values of parameters that exist at previous points in time or magnitudes computed from these values. The writing device 48 is configured in particular to determine or to compute median values, minimal values, and/or maximum values of parameters for time intervals of predetermined or variable length.

In addition, the writing device 48 can be configured to determine or to compute, for the end of such a time interval or for another point in time, time integrals of parameters for a period from a given reference time point in the past (for example, the production or implementation of a device 14) up to the point in time. The writing device 48, in addition, can be configured to determine the start, duration, and end of the stipulated time interval on the basis of determined conditions.

The writing device 48 can be configured I such a way that it undertakes only writing operations and no reading operations at the storage unit 50. This measure can also serve to prevent data from the storage unit 50 from disturbing the medical network 10.

The storage unit 50 includes a non-temporary storage device 52 and a temporary storage device 54. The non-temporary storage device 52 includes, for example, a hard drive or other non-temporary magnetic or optical storage medium. The temporary storage device 54 includes, for example, an RAM or other semiconductor storage device.

The writing device 48 and the storage unit 50 are, in particular, configured to write current data in the temporary storage device 54 and historical data in the non-temporary storage device 52 of the storage unit 50.

The non-medical area 60 of the bridge apparatus 30 includes a reading device 62. An input of the reading device 62 is coupled with an output of the storage unit 50. For reading out data from the storage unit 50, to indicate that the reading device 62 must convey to the storage unit 50 in a read message which data are to be read out, between the reading device 62 and the storage unit 50 two arrows are shown in opposite directions. The reading device 62 can be configured to perform or permit no other access to the storage unit 50 than reading access, in particular no writing access. Even with this measure it is possible to prevent data from the storage unit 50 from disturbing the medical network 10. The reading device 62 can, in addition, be configured to prepare data read by the storage unit 50, for example to connect them with one another logically or algebraically.

The non-medical area 60 of the bridge apparatus 30 includes, in addition, an authentication device 64 and a data output 66 to couple the bridge apparatus 30 with the non-medical network 20. The authentication device is coupled with the reading device 62 and the data output 66. The authentication device 64 is configured to review access requests from the non-medical network 20 to the bridge apparatus 30 and in particular to the storage unit 50 with respect to identity and/or authorization of the requesting user and to verify identity and authorization. Only access requests from users from the non-medical network 20 whose authorization is verified are forwarded to the reading device 62.

The authentication device 64, in addition, can be configured to verify every access request from the non-medical network 20 via the data output 66 to the bridge apparatus 30 to determine whether the request is for reading access or a read message or read command and to discard or ignore any other request. As a result of this configuration of the authentication device 64, it is possible to prevent a desired or undesired disabling of the bridge apparatus 30 and a disabling of the medical network 10 via the bridge apparatus 30 from the non-medical network 20.

The data input 42 and data reception device 44 or the data input 42, data reception device 44 and writing device 48 constitute a first interface device for coupling the storage unit 50 with the medical network 10. The writing device 48 or part of the writing device 48, the storage unit 50 and the reading device 62 or part of the reading device 62 constitute a database system or are components of a database system. Alternatively the storage unit 50 constitutes a database system or the storage unit 50 includes a database system. The authentication device 64 and data output 66 or the reading device 62, authentication device 64 and data output 66 constitute a second interface device for coupling the storage unit 50 with the non-medical network 20.

Altogether, the bridge apparatus 30 is configured to receive data on devices 14 via the medical network 10 and the data input 42 and to write them as current data and as (optionally prepared as described above) historical data in the storage unit 50 and to receive inquiries on devices 24 via a non-medical network 30 and a data output 66 and to answer them by reading from data from the storage unit 50. For this purpose the non-medical area 60 of the bridge apparatus makes available, for example, Web-based services for communication that can be addressed from the non-medical network and can be used after authentication.

The second interface device, in particular the authentication device 64 and reading device 62, can be configured to allow data filed in the storage unit 50 to be subscribed or polled by the non-medical network 20.

Figure 2:
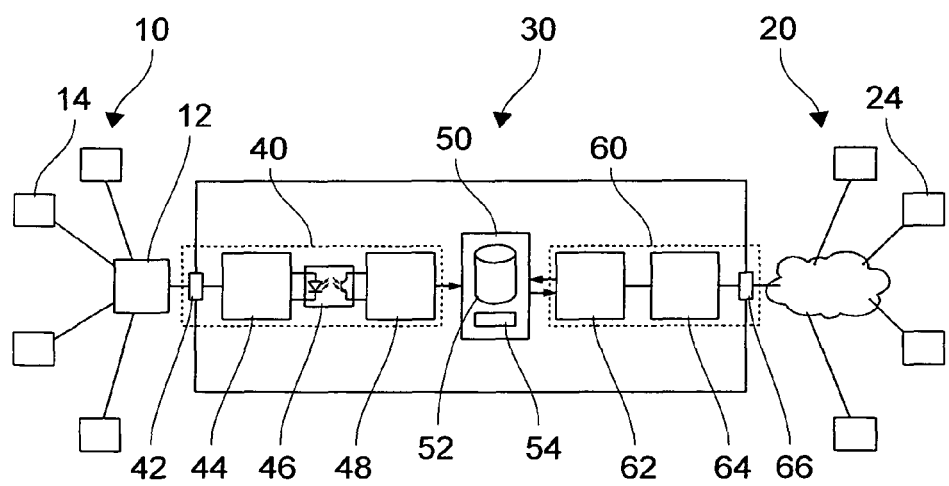
FIG. 2 shows a schematic depiction of an additional bridge apparatus.

FIG. 2 shows a schematic depiction of a medical network 10 and a non-medical network 20, which are coupled with one another via an additional bridge device 30. The bridge apparatus 30 shown in FIG. 2 is distinguished from the bridge apparatus presented above with reference to FIG. 1 in that between the data input 42 and the storage unit 50 of the bridge apparatus 30 a device 46 for coupling in only one direction is positioned, which physically allows data transmission only in one direction. The device 46 allows in particular data transmission from the data input 42 to the storage unit 50, but not the reverse.

The device is, for example, depicted as a one-way optical coupler 46 whose input is coupled with the output of the data reception device 44 and whose output is coupled with the input of the writing device 48. A device that physically allows data transmission in only one direction can also be positioned at another site between the data input 42 and the storage unit 50. For example, the device 46, contrary to the illustration in FIG. 2, can be positioned between the data input 42 and the data reception device 44. The device 46 prevents with absolute security an intentional or unintentional disruption of the medical network 10 from the non-medical network 20. The device 46 can be a component of the second interface device.

Figure 3:
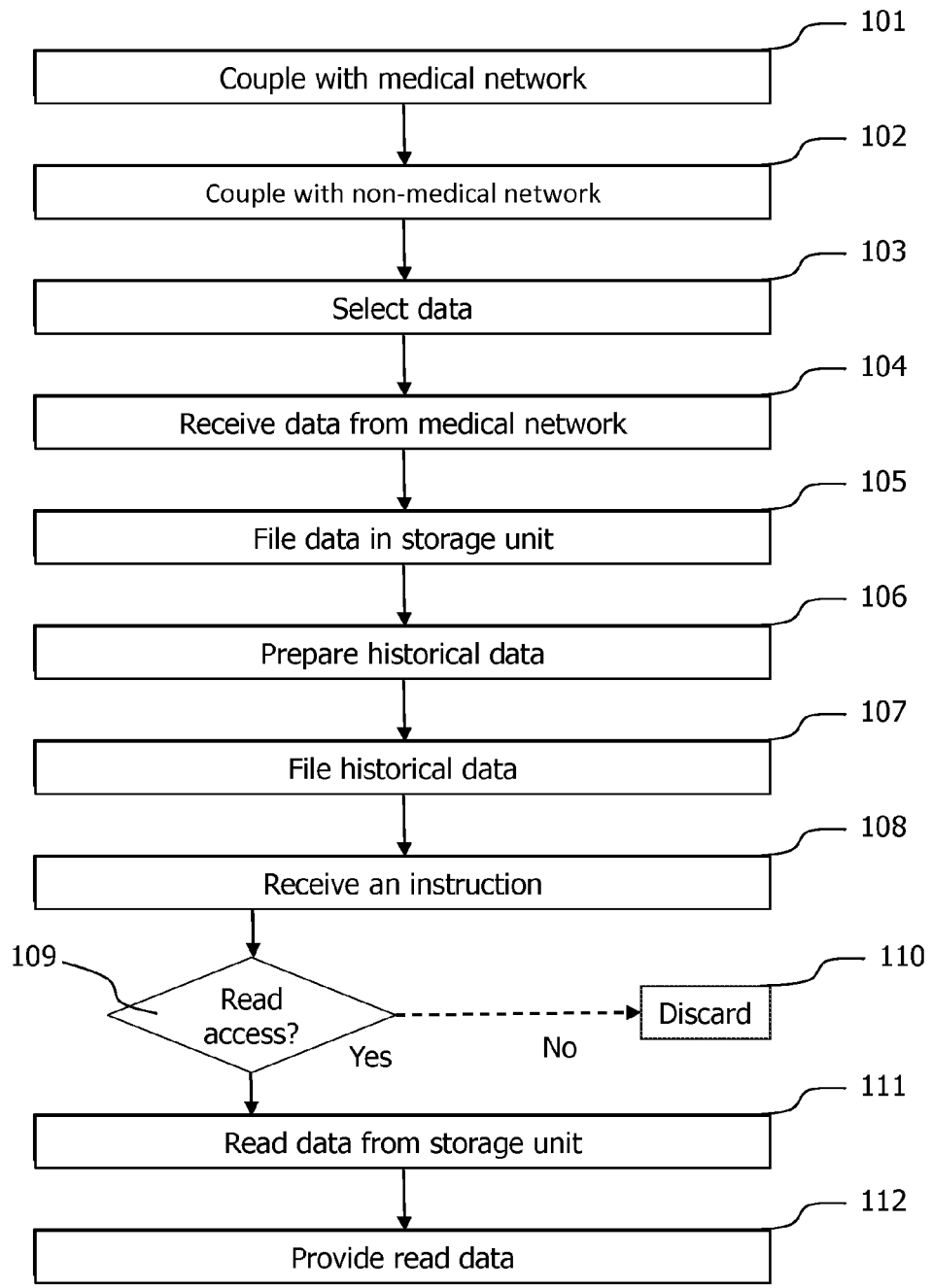
FIG. 3 shows a schematic depiction of a method for providing data from a medical network in a non-medical network.

FIG. 3 shows a schematic flow diagram of a method to provide data from a medical network in a non-medical network. Although the method can also be performed with apparatuses that differ from the apparatuses presented above with reference to FIGS. 1 and 2, in the following, reference numbers from FIGS. 1 and 2 are used by way of example to facilitate comprehension.

In a first step 101, a bridge apparatus 30 is coupled with a medical network 10 via a first interface device 42, 44, 46, 48. In a second step 102, the bridge apparatus 30 is coupled with a non-medical network 20 via a second interface device 62, 64, 66 of the bridge apparatus 30.

In an optional third step 103, data from the medical network 10 or from devices 14 from the medial network 10 are selected that are to be stored in a storage unit 50 of the bridge apparatus 30. This occurs in particular by means of a user interface that is coupled via the medical network 10 or directly with the bridge apparatus 30 or its medical area 40. To the extent that the medical area 40 of the bridge apparatus 30 is considered part of the medical network 10, the user interface is also in both cases part of or a participant in the medical network 10.

In a fourth step 104, the bridge apparatus 30, via the first interface device 42, 44, 46, 48, receives data from the medical network 10, in particular from one or more devices 14 in the medical network. The data include in particular the values of parameters that are selected, controlled, or measured by the devices 14. In a fifth step 105, the data received in the fourth step 104 are filed in the storage unit 50 of the bridge apparatus 30, in particular in a temporary storage device 54 of the storage unit 50.

In a sixth step 106, the data received in the fourth step 104, in particular together with data received previously, are prepared as historical data. In the process, for a parameter, for example, a median value, a minimum value, a maximum value within a time interval and a time integral value from a predetermined reference time point in the past until the end of the time interval are computed. In a seventh step 107, the historical data prepared in the sixth step 106 are filed in the storage unit 50, in particular in a non-temporary storage device 52 of the storage unit 50.

Both the current data and the historical data can be provided with a time stamp before filing or writing in the storage unit 50. Filed in the storage unit 50 with the historical data are, in particular, the start and end of the particular time interval or a reference point within the time interval (for example, start or end date of the time interval) and the length of the time interval. All data can be filed in the storage unit 50 together with associated time stamps without the aforementioned preparation as historical data.

The fourth step 104, fifth step 105, sixth step 106, and seventh step 107 are, in particular, repeated at a predetermined period or with a predetermined frequency. Alternatively, these steps can be executed depending on predetermined conditions or controlled by the occurrence of predetermined events. The fourth step 104, fifth step 105, sixth step 106, and seventh step 107 can be executed for each parameter independently or for several or all parameters synchronously.

In an eighth step 108, the bridge apparatus 30 receives an instruction or command via the data output 66. In a ninth step 109, verification is performed as to whether the instruction received in the eighth step 108 is a reading access request. If it is not a reading access request, and in particular if it is a writing access request, the instruction is discarded or ignored in a tenth step 110.

If the instruction received in the eighth step is a reading access request, the data corresponding to the reading access request are read out of the storage site 50 in an eleventh step 111 and provided in a twelfth step 112 at the data output 66 in the non-medical network.

In the method presented with reference to FIG. 3, a communication can proceed as follows between a device 24 or a user or a client from the non-medical network 20 on the one hand and from the bridge apparatus 30 on the other hand. Before the eighth step 108, the device 24 reports itself by means of client software at the bridge apparatus 30 and is optionally authenticated by the authentication device 64. The bridge apparatus 30 responds with a token, which is used in the ensuing communication by the client software of the device 24. The bridge apparatus 30 transmits information to the device 24 on the data filed in the storage site 50 and thus available for the device 24.

The device 24 or its user can select data from available data via the client software. Said data are called up once (for example, by means of polling) by the bridge apparatus or subscribed (for example, by means of a method similar to the subscribing described above). Available data here include both current data as well as historical data. If static data are requested such as median value, minimum value, or maximum value within a period that includes several time intervals, then such data can be computed by the bridge apparatus or by the client software from the corresponding data of the individual time intervals within the period.

An example of a device 24 in the non-medical network 20 is a so-called dashboard, which can be positioned inside an operating room or else outside it, for example in a listening room or in a work room for medical staff. All data important or relevant for observing or monitoring an operation can be displayed on the dashboard. These important or relevant data include, for example, patient data, anesthesia data, or current data on devices 14 in the medical network 10.

The invention claimed is:

1. A bridge apparatus for coupling a medical network with a non-medical network, comprising:

a storage unit for storing data from the medical network, the storage unit including a temporary storage device and a non-temporary storage device;

a first interface device for coupling the storage unit with the medical network, the first interface device including
a writing device for writing data from the medical network into the storage unit,
a data input for coupling the writing device with the medical network, and
a data reception device for emitting and receiving electromagnetic signals or light signals in the infrared range, the data reception device coupled to the data input and configured to subscribe to data on the medical network and retrieve in the medical network the values of predefined parameters at predetermined times or at predetermined time intervals or upon the existence of predetermined conditions of devices; and a second interface device for coupling the storage unit with the non-medical network, the second interface device including
a reading device for reading data from the storage unit,
a data output for coupling the reading device with the non-medical network, and
an authentication device coupled with the reading device and the data output, where the bridge apparatus is configured to execute at least one of write-only access requests to the storage unit via the first interface device, and read-only access requests to the storage unit via the second interface device, wherein the bridge apparatus is configured to store current data exclusively in the temporary storage device and historical data exclusively in the non-temporary storage device and the bridge apparatus is configured to issue the current data and the historical data to the non-medical network via the second interface device.

2. The bridge apparatus of claim 1, wherein the first interface device is configured exclusively for writing access requests to the storage unit.

3. The bridge apparatus of claim 1, further comprising:
a device to provide data received via the first interface device, where the device is configured to determine at least one of a median value, a time integral or an extreme value within a predetermined time interval.

4. The bridge apparatus of claim 1, wherein the bridge apparatus is configured to provide data received via the first interface device with a time stamp.

5. The bridge apparatus of claim 1, wherein the bridge apparatus is configured to archive or document data on an operation.

6. The bridge apparatus of claim 1 configured in order to release no error message into the medical network.

7. The bridge apparatus of claim 1, wherein the second interface device is configured exclusively for reading access requests to the storage unit.

8. The bridge apparatus of claim 1 configured in order to suppress every error message from a predetermined group of error messages to recipients in the medical network.

9. The bridge apparatus of claim 1, further comprising a user interface.

10. The bridge apparatus of claim 9, wherein the user interface includes a screen, a keyboard and a computer mouse.

11. The bridge apparatus of claim 9, wherein the user interface is coupled with the bridge apparatus directly or via the medical network.

12. The bridge apparatus of claim 11, wherein if the user interface is coupled with the bridge apparatus via the medical network, the data reception device includes an operating mode in which the communication of the bridge apparatus with the user interface is allowed via the data input.

13. The bridge apparatus of claim 1, wherein the data reception device suppresses each issuing or each emission of data via the data input into the medical network.

14. The bridge apparatus of claim 1, wherein the data reception device emits only commands or instructions from a predetermined group of commands or instructions via the data output into the medical network.

15. The bridge apparatus of claim 1, wherein the data reception device emits at predetermined time intervals at most a predetermined maximum number of commands or instructions via the data input into the medical network.

16. The bridge apparatus of claim 1, wherein the data reception device emits no commands or instructions via the data input into the medical networks.

17. The bridge apparatus of claim 1, wherein the data reception device is configured to ignore commands and instructions received from the medical network or all commands and instructions from a predetermined group of commands and instructions.

18. The bridge apparatus of claim 1, wherein the data reception device is configured to reply to instructions or commands in predetermined, secure manner.

19. The bridge apparatus of claim 1, wherein the bridge apparatus archives or documents data to contribute to quality control of the data.

20. The bridge apparatus of claim 1, wherein the temporary storage unit includes a multiple-writable storage unit with RAM and the non-temporary storage unit includes a hard disk or another magnetic or optical storage medium or solid-state drive.

21. A method for providing data from a medical network to a non-medical network, comprising the following steps:
   coupling a bridge apparatus with a medical network via a first interface device of the bridge apparatus, the first interface device including a writing device for writing data from the medical network into a storage unit including a temporary storage device and a non-temporary storage device, a data input for coupling the writing device with the medical network, and a data reception device for emitting and receiving electromagnetic signals or light signals in the infrared range, the data reception device coupled to the data input and configured to subscribe to data on the medical network and retrieve in the medical network the values of predefined parameters at predetermined times or at predetermined time intervals or upon the existence of predetermined conditions of devices;
   coupling the bridge apparatus with a non-medical network via a second interface device of the bridge apparatus, the second interface device including a reading device for reading data from the storage unit, a data output for coupling the reading device with the non-medical network, and an authentication device coupled with the reading device and the data output;
   receiving data from the medical network via the first interface device;
   writing the received data to a storage location of a storage unit of the bridge apparatus;
   reading data from the storage unit; and
   providing data read by the storage unit to the second interface,
   wherein the bridge apparatus is configured to store current data exclusively in the temporary storage device and historical data exclusively in the non-temporary storage device and the bridge apparatus is configured to issue the current data and the historical data to the non-medical network via the second interface device.

22. A method of claim 21, further comprising at least one of the following steps:
   selecting data from the medical network that are to be stored in the storage unit at a user interface in the medical network;
   receiving a read message via the second interface device;
   discarding a read message received via the first interface device;
   discarding a write message received via the second interface device;
   verifying an instruction received via the second interface device and discarding the instruction if it is not a read message;
   preparing historical data; and
   writing historical data into the storage unit.

23. The method of claim 21, wherein the method is executed by a computer program with program code that is run on at least one of a computer and a processor.

24. A bridge apparatus for coupling a medical network with a non-medical network, comprising:
   a storage unit for storing data from the medical network, the storage unit including a temporary storage device and a non-temporary storage device;
   a first interface device for coupling the storage unit with the medical network, the first interface device including
      a writing device for writing data from the medical network into the storage unit,
      a data input for coupling the writing device with the medical network,
      a data reception device coupled to the data input,
      an optical coupler between the data reception device and the writing device, the optical coupler only allowing data transmission from the data input to the storage, but not the reverse; and
   a second interface device for coupling the storage unit with the non-medical network, the second interface device including a reading device for reading data from the storage unit, a data output for coupling the reading device with the non-medical network, and an authentication device coupled with the reading device and the data output,
   where the bridge apparatus is configured to execute at least one of write-only access requests to the storage unit via the first interface device, and read-only access requests to the storage unit via the second interface device,
   wherein the bridge apparatus is configured to store current data exclusively in the temporary storage device and historical data exclusively in the non-temporary storage device and the bridge apparatus is configured to issue the current data and the historical data to the non-medical network via the second interface device.

25. The bridge apparatus of claim 24, further comprising a user interface.

26. The bridge apparatus of claim 25, wherein if the user interface is coupled with the bridge apparatus via the medical network, the data reception device includes an operating mode in which the communication of the bridge apparatus with the user interface is allowed via the data input.

27. The bridge apparatus of claim 24, wherein the data reception device emits only commands or instructions from a predetermined group of commands or instructions via the data output into the medical network.

28. The bridge apparatus of claim 24, wherein the data reception device emits at predetermined time intervals at most a predetermined maximum number of commands or instructions via the data input into the medical network.

29. The bridge apparatus of claim 24, wherein the data reception device is configured to ignore commands and instructions received from the medical network or all commands and instructions from a predetermined group of commands and instructions.

30. The bridge apparatus of claim 24, wherein the optical coupler prevents data transmission as signals are suppressed or sealed off.

31. The bridge apparatus of claim 24, wherein the data transmission is logically decoupled by the optical coupler.

* * * * *